(12) United States Patent
Bridges et al.

(10) Patent No.: US 7,718,841 B2
(45) Date of Patent: May 18, 2010

(54) EXTRACTIVE DISTILLATION

(75) Inventors: Joseph P. Bridges, Houston, TX (US);
Robert J. Haynal, Houston, TX (US);
Allen David Hood, Jr., Houston, TX (US); Solon B. Williams, Kingwood, TX (US)

(73) Assignee: Equistar Chemicals, LP, Houston, TX (US)

( * ) Notice: Subject to any disclaimer, the term of this patent is extended or adjusted under 35 U.S.C. 154(b) by 192 days.

(21) Appl. No.: 12/157,300

(22) Filed: Jun. 9, 2008

(65) Prior Publication Data

US 2009/0306450 A1    Dec. 10, 2009

(51) Int. Cl.
*C07C 7/08* (2006.01)
*C07C 7/10* (2006.01)

(52) U.S. Cl. .............. 585/810; 585/833; 585/834; 585/836; 585/838; 585/860

(58) Field of Classification Search ............... 585/833, 585/810, 834, 836, 838, 860, 861
See application file for complete search history.

(56) References Cited

U.S. PATENT DOCUMENTS

| | | | |
|---|---|---|---|
| 2,993,841 A | 7/1961 | Sarno | 202/39.5 |
| 3,436,438 A | 4/1969 | Takao et al. | 260/681.5 |
| 4,134,795 A | 1/1979 | Howat, III | 203/53 |

*Primary Examiner*—Tam M Nguyen
(74) *Attorney, Agent, or Firm*—Dennis M. Kozak

(57) ABSTRACT

A method for reducing corrosion in a diolefin extractive distillation process comprising preventing the formation of ammonium carbonate by promoting the formation of a carbonate salt that does not dissociate in the ammonium carbonate dissociation temperature range of that extractive distillation process.

9 Claims, 2 Drawing Sheets

EXTRACTIVE DISTILLATION

BACKGROUND OF THE INVENTION

1. Field of the Invention

This invention relates to the solvent extraction of a diolefin from a mixture of hydrocarbons. More particularly, this invention relates to the extractive distillation of butadiene or isoprene from a mixture of hydrocarbons.

2. Description of the Prior Art

Thermal cracking of hydrocarbons is a petrochemical process that is widely used to produce olefins such as ethylene, propylene, butenes, butadiene, and aromatics such as benzene, toluene, and xylenes.

An olefin production plant is generally composed of a cracking unit and a hydrocarbons unit.

In the cracking unit a hydrocarbonaceous feedstock such as ethane, naphtha, gas oil, or other fractions of whole crude oil is mixed with steam which serves as a diluent to keep the hydrocarbon molecules separated.

This mixture, after preheating, is subjected to hydrocarbon thermal cracking using elevated temperatures (1,450 to 1,550 degrees Fahrenheit or F.) in a pyrolysis furnace (steam cracker or cracker). This thermal cracking is carried out without the aid of any catalyst.

The cracked product effluent of the pyrolysis furnace (furnace) contains hot, gaseous hydrocarbons of great variety (from 1 to 35 carbon atoms per molecule, or C1 to C35 inclusive, both saturated and unsaturated). This product contains aliphatics (alkanes and alkenes), alicyclics (cyclanes, cyclenes, and cyclodienes), aromatics, and molecular hydrogen (hydrogen).

This furnace product is then subjected to further processing in the cracking unit to produce, as products of the olefin plant, various, separate and individual product streams such as hydrogen, ethylene, propylene, fuel oil, and pyrolysis gasoline. After the separation of these individual streams, the remaining cracked product contains essentially C4 hydrocarbons and heavier. This remainder is fed to a debutanizer wherein a crude C4 stream is separated as overhead while a crude C5 and heavier stream is removed as a bottoms product and further processed in a depentanizer.

The crude C4 stream can contain varying amounts of n-butane, isobutane, 1-butene, 2-butenes (both cis and trans isomers), isobutylene, acetylenes, and diolefins such as butadiene (1,2-, 1,3-., cis, and trans isomers), vinyl acetylene, and ethyl acetylene, all of which are known to boil within a narrow range, U.S. Pat. No. 3,436,438. Further, some of these compounds can form an azeotrope. Crude C4's are, therefore, known to be difficult to separate by simple thermal distillation.

The crude C5 stream can contain isoprene, pentanes, pentenes, hexanes, hexenes, and aromatics such as benzene, toluene, and xylenes, and can also be difficult to separate by simple thermal distillation.

The crude C4 and C5 streams are normally further processed in the hydrocarbons unit for the separation of other individual product streams such as butenes, butadiene, isoprene, benzene, toluene, and the like.

The crude C4 stream, after removal of acetylenes, normally goes to a butadiene extraction unit for, among other things, the separation and recovery of butadiene therefrom.

The crude C5 stream is normally sent to an isoprene extraction unit for, among other things, the separation and recovery of isoprene therefrom.

A dominating commercial process for separating butadiene from C4's or isoprene from C5's is known technically as "fractional extraction" but is more commonly referred to as "solvent extraction" or "extractive distillation." However it is termed, this diolefin separation process employs the technique of altering the relative volatilities of various of the compounds to make easier the separation of those compounds by thermal fractional distillation. More specifically, this process employs an aprotic polar compound (solvent) that has a high complexing affinity toward the more polarizable butadiene or isoprene molecules than, and to the substantial exclusion of, the other olefins in the crude C4 or C5 streams. Known solvents used in this process include acetonitrile, dimethylformamide, furfural, N-methyl-2-pyrrolidone, acetone, dimethylacetamide, and the like. This process and the solvents used in it are well known, U.S. Pat. Nos. 2,993,841 and 4,134,795.

The primary equipment employed in the extractive distillation of butadiene or isoprene from a crude stream is an extractive distillation tower or series of towers followed by a diolefin thermal stripping tower and a separate solvent thermal stripping tower. As will be described in greater detail hereinafter, certain equipment that is ancillary to these towers has, from time to time, been plagued with premature and severe corrosion damage. The corrosion rates experienced have been on the order of about 500 mils per year when typical corrosion rates would have been 1 to 2 mils per year.

Until the advent of this invention, the source of this periodic corrosion problem was unknown, and the corrosion itself was difficult to control because the source of the problem was unknown and the corrosion rate was drastic. Pursuant to this invention, the root cause of this corrosion problem has been discovered and removed in an efficient and cost effective manner.

SUMMARY OF THE INVENTION

Pursuant to this invention, it has been found that the source of the aforesaid corrosion problem in the extractive distillation of butadiene or isoprene was the combination of 1) the presence of ammonia and carbon dioxide in various process streams, coupled with 2) certain operating conditions in the extractive distillation process. It was surprisingly found that elements 1) and 2) aforesaid worked together to keep captive in the process any ammonium carbonate salt that formed from the ammonia and carbon dioxide present in the process.

Due to a unique confluence of normal operating conditions in this process, which conditions will be explained hereinafter, it was discovered that ammonium carbonate salt was not removed with any of the streams that are normally removed from the process. Ammonium carbonate was discovered to largely be kept captive in the process, thereby ultimately causing, again due to the process operating conditions, a buildup of that salt in certain ancillary equipment. Because this salt is corrosive and was never allowed to leave the process, the buildup of salt deposits continued in certain of the equipment to a catastrophic level, thereby causing premature corrosion in, and even failure of that equipment.

BRIEF DISCUSSION OF THE DRAWINGS

DETAILED DESCRIPTION OF THE INVENTION

For sake of brevity and clarity, this invention is described in detail hereinafter in respect of the extractive distillation of butadiene. However, this invention applies as well to the extractive distillation of isoprene. Once apprised of the details of this invention, as set forth herein, regarding the extractive distillation of butadiene, one skilled in the art can readily, and without more, apply this invention to the extractive distillation of isoprene. For example, the flow scheme and equipment shown in the Figures described herein below can be applied to isoprene instead of butadiene.

Figure 1:
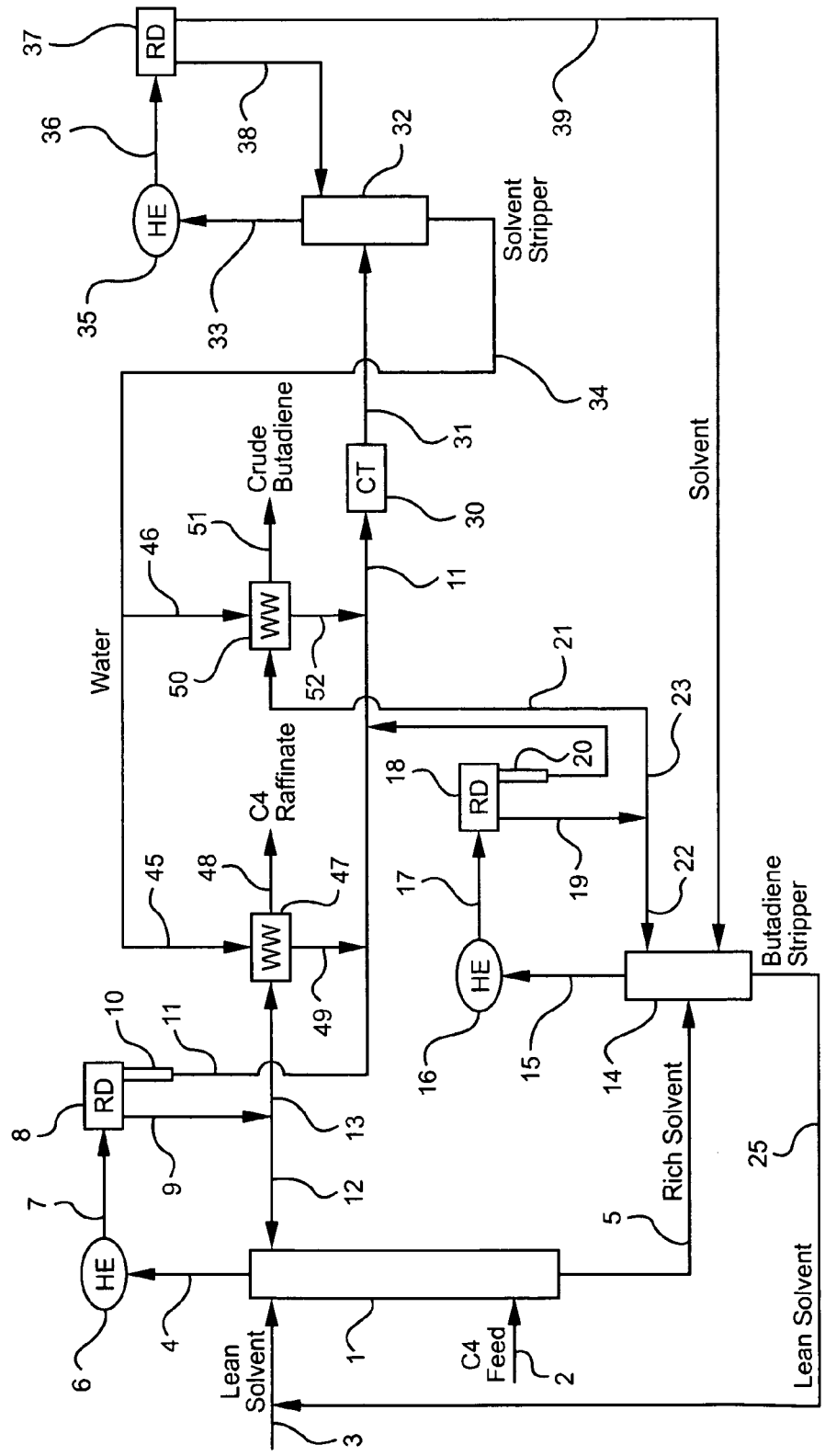
FIG. 1 is a flow diagram of a typical commercial diolefin extraction process.

FIG. 1 shows an extractive distillation tower (column) 1 that receives, at a lower level along the height of the tower, crude C4 feed stream 2, and, at an upper level of the tower, a lean solvent stream 3. The term "lean solvent" means a solvent stream that contains little or no (essentially no) butadiene (or isoprene). Tower 1 can be a single tower as shown in FIG. 1 or two towers operating in series (not shown), as desired. In tower 1, streams 2 and 3 are contacted at an elevated temperature with one another in counter current flow to allow the solvent in stream 3 to extract butadiene from stream 2.

A crude C4 stream 4 (first stream) containing little or no butadiene is removed overhead from tower 1 at a temperature of at least about 125 F, and passed to a tube and shell heat exchanger 6. In exchanger 6, stream 4 is cooled to a temperature of less than about 100 F. Cooled stream 4, i.e., stream 7, is passed to a recycle drum 8 wherein it is collected for water separation and for distribution purposes. Drum 8 has operatively associated therewith, a water leg 10 which primarily collects water, but which can contain small, but significant, amounts of solvent and C4's, and from which is taken stream 11 (third stream).

A bottoms solvent stream 5 (second stream) that is rich in butadiene, e.g., containing a substantial, if not major, amount of butadiene, is removed from the bottom of tower 1. Tower 1 has a typical bottoms reboiler circuit for heating and returning a portion of stream 5 to the tower. This circuit is known in the art, and is not shown in FIG. 1 for sake of simplicity only. The normal operating temperature for the bottom of tower 1 is at least about 245 F. Butadiene rich stream 5 is fed to a thermal distillation tower 14 to strip butadiene from its associated solvent.

An essentially butadiene free, cooled crude C4 stream 9 is removed from drum 8 and split to provide a reflux stream 12 that is returned to the interior of tower 1, and a separate stream 13 that is passed to a water wash unit 47. In unit 47, stream 13 is water washed with clean water stream 45 to produce a C4 raffinate product stream 48 that is removed from the process for further processing elsewhere. Water wash 47 also produces a separate stream 49 that is primarily a water stream, but can contain minor amounts (amounts that are worth the effort of reclaiming) of solvent and hydrocarbons (e.g., C4's and/or butadiene).

Butadiene rich solvent stream 5, containing a substantial, if not major, amount of butadiene, is passed into butadiene stripper tower 14 (first thermal stripping tower) and therein heated to separate butadiene from its associated solvent. Tower 14 is operated at a temperature of at least about 278 F to form a bottoms stream 25 (fifth stream) that is essentially lean solvent suitable for return to lean solvent stream 3 and reuse in tower 1 to extract additional butadiene from fresh, incoming feed 2. Butadiene rich overhead stream 15 (fourth stream) from tower 14 is passed to a heat exchanger 16, like that of unit 6.

In exchanger 16, stream 15 is cooled to a temperature below about 100 F., and passed as cooled stream 17 to a reflux drum 18 wherein it is collected for water separation and for distribution purposes. Drum 18 has associated therewith a water leg 20 that operates in a manner similar to leg 10 in that it primarily collects water. In the case of leg 20, water stream 21 (sixth stream) that is removed from that leg can contain small, but significant, amounts of solvent and butadiene, particularly solvent, that are worth the effort of reclaiming.

Butadiene rich stream 19 is removed from drum 18, passed in part as reflux stream 22 to tower 14, and passed in part as stream 23 to a separate water wash unit 50. In unit 50, stream 23 is contacted with clean water from line 46. A washed crude butadiene stream 51 that can contain C5 and heavier materials is removed from the process as a product stream to be further treated elsewhere. Water stream 52 can contain hydrocarbons (e.g., butadiene) and solvent in minor amounts that are worth recovering.

As desired, one or more or all of streams 21, 49, and 52 can be combined with stream 11.

Streams 11, 21, 49, and/or 52 can be passed to, and combined in, collection tank 30, and, then removed from tank 30 as single, combination stream 31.

Stream 31 is passed to a separate thermal distillation tower 32 (second thermal stripping tower) that is operated to thermally strip solvent plus any associated hydrocarbons (C4's+) from water. Tower 32 is operated with a bottoms temperature of at least about 250 F. to provide a clean (essentially hydrocarbon free) water stream 34 (eighth stream) that is used to provide wash water to streams 45 and/or 46. In this manner, tower 32 produces an overhead stream 33 (seventh stream) that can contain water, solvent, and one or more C4 and heavier hydrocarbons.

Stream 33 is passed to a heat exchanger 35, like that of unit 6. In exchanger 35, stream 33 is cooled to a temperature of no more than about 120 F. to produce stream 36. Cooled stream 36 can contain, for example, water, solvent, one or more C4 and heavier hydrocarbons, and is passed to a reflux drum 37 for collection and for distribution purposes. A reflux stream 38 is removed from drum 37 and returned to the interior of tower 32. A separate stream 39 (ninth stream) is removed from drum 37 and returned to tower 14 for recovery of solvent and hydrocarbons that may be carried by that stream.

Pursuant to this invention, it has been found that fugitive ammonia and carbon dioxide can reach the interior of towers 1, 14, and/or 32. It has further been found that, although ammonia and carbon dioxide could theoretically be purged from the process by way of vents on reflux drums 8 and 18, this was not, in fact, what was occurring.

It was surprisingly found that the operating temperature of each of towers 1, 14, and 32 was such that any ammonium carbonate salt formed from the fugitive ammonia and carbon dioxide present in these towers was dissociated by their operating, e.g., bottom, temperatures so that essentially all the ammonia and carbon dioxide present in each tower was passed out of the tower as vapor in its overhead stream, i.e., streams 4, 15, and 33. It should be understood that in a commercial process such as the one described in FIG. 2, the dissociation temperature of ammonium carbonate is not a precise temperature as would be found in the pristine environment of a chemical laboratory. It was found that this dissociation temperature varied widely depending on the location of the ammonium carbonate in the process of FIG. 2. For example, the dissociation temperature of ammonium carbonate was affected substantially by the presence or absence of other chemical constituents present at a particular location in the process of FIG. 2. Accordingly, it was found that the dissociation temperature range to be used in the practice of this invention is from about 120 to about 140 F., the precise laboratory dissociation temperature of 136 F. notwithstanding. If one operated on the premise that ammonium carbonate dissociated essentially at 136 F., this invention would not have been discovered. For example, one skilled in the art would not have expected dissociated ammonium carbonate to be present at the 125 F. overhead temperature of tower 1, but it was.

It was further found that the operating temperature of the heat exchangers for each such tower, i.e., exchangers 6, 16, and 35, was such that the formation of ammonium carbonate from ammonia and carbon dioxide was promoted. This caused a preferential deposition of ammonium carbonate solely in those heat exchangers and was found to be the proximate cause of the premature corrosion and catastrophic failures those exchangers were, from time to time, experiencing Because towers 1, 14, and 32 conventionally operate at a temperature that promotes the dissociation of ammonium carbonate to ammonia and carbon dioxide vapor, any and all ammonia and carbon dioxide that reached the process in general, and these towers in particular, was preferentially forced into overhead streams 4, 15, and 33, and, therefore, into their associated overhead heat exchangers 6, 16, and 33. Accordingly, all fugitive ammonia and carbon dioxide that reached the process was inadvertently perpetually kept captive in the process as a soluble solution from water boots and water wash towers that fed tower 32 and recycled back to tower 14 by way of line 39 or as an ammonium carbonate deposition on the cooler internal surfaces in heat exchangers 6, 16, and 33, i.e., exchanger internal surfaces that were below the temperature at which ammonium carbonate dissociates.

The fugitive ammonia and carbon dioxide can be present in feed 2 as it enters the process and/or can be generated in situ in the process. For example, it has been found that certain of the solvents such as acetonitrile can produce some ammonia under the operating conditions of the solvent extraction process itself.

Further pursuant to this invention, it has been found that the fugitive carbon dioxide in the solvent extraction process can be converted 1) to a stable carbonate salt that will not dissociate at the operating, particularly the operating, temperatures of towers 1, 14, and 32, and 2) to the substantial exclusion of the formation of ammonium carbonate.

This stable carbonate salt that is not dissociated under the operating conditions of the process can then be removed from the process by way of a purge stream, thereby 1) freeing what would otherwise be perpetually captive ammonia and carbon dioxide, and 2) removing the fugitive carbon dioxide from the process itself. The fugitive ammonia vapor is thereby left as ammonia gas via vents on reflux drums 8 and 18 or in a separate purge stream as well.

The stable salt of this invention can be formed by adding at least one base compound to at least one stream in the extractive distillation process in an amount sufficient to form the desired stable salt, to the essential (substantial) exclusion of the formation of the unstable ammonium carbonate salt.

The stable carbonate salt of this invention can be formed by adding to the process at least one of sodium hydroxide or potassium hydroxide in an amount of from about 4 parts per million (ppm) to about 0.4 weight percent based on the total weight of the stream being treated.

Figure 2:
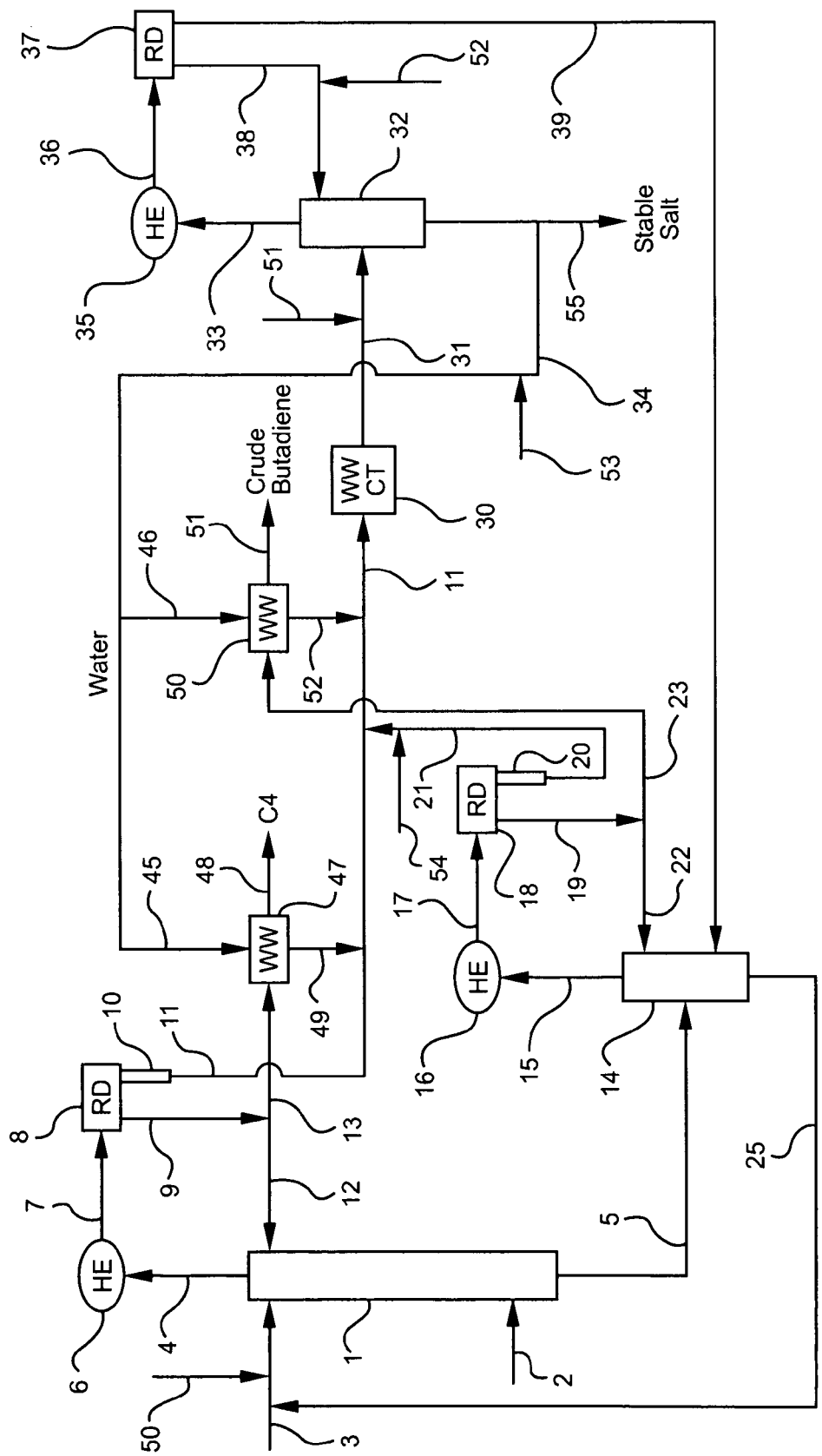
FIG. 2 is the flow diagram of FIG. 1 modified pursuant to this invention.

FIG. 2 shows the process of FIG. 1 modified pursuant to this invention. FIG. 2 shows that the base compound or compounds used to form the desired stable carbonate salt can, by way of example, be added to one or more or all of solvent stream 3 by way of conduit 50, to feed stream 31 by way of conduit 51, to reflux stream 38 by way of conduit 52, to water stream 34 by way of conduit 53, and to water stream 21 by way of conduit 54. The compound(s) added to the process can be inserted into the process in streams and equipment other than that shown in FIG. 2 and still fall within the scope of this invention.

The primary goal of this invention is to add such at least one base compound to one or more locations in the process in an aggregate (total) amount that is sufficient to prevent the formation of ammonium carbonate to any significant extent in the extractive distillation process as a whole. Extractive distillation processes and equipment configurations in various plants can vary from that shown in FIG. 2 so that it is impossible to specify all the points of introduction of the ammonium carbonate preventing base compound(s), or the total amount of such compound(s) that should be added to achieve the inventive results of this invention. However, once apprised of this disclosure, one skilled in the art will readily be able to determine where and in what amount to inject the ammonium carbonate suppressing base compound(s) in a specific process to achieve the desired results of this invention.

FIG. 2 also shows that the stable carbonate salt formed pursuant to this invention, and the carbon dioxide it ties up, can be removed from the extractive distillation process completely by way of a water purge stream 55 from bottoms stream 34 of tower 32. Other removal sites can be used, and will be obvious to one skilled in the art.

EXAMPLE

A process as shown in FIG. 2 was carried out in a commercial butadiene solvent extraction process.

Feed stream 2 for extractive distillation tower 1 contained about 2 ppm ammonia and about 5 ppm carbon dioxide.

Sodium hydroxide solution is contacted with feed stream 2 in the amount of about 4,000 ppm, based on the total weight of stream 2.

Within one month of operation using bottom temperatures for towers 1, 14, and 32 of about 245 F., about 278 F., and about 250 F., respectively, no ammonium carbonate was formed in any of heat exchangers 6, 16, and 35.

We claim:

1. A process wherein a diolefin selected from the group consisting of butadiene and isoprene is separated from a mixture containing at least one monoolefin, said diolefin, carbon dioxide, and ammonia using an extractive distillation step that employs a diolefin lean solvent that has a complexing affinity for said diolefin to the substantial exclusion of said at least one monoolefin, said process comprising subjecting said mixture to said extractive distillation step to form a first stream (4) containing essentially said at least one monoolefin, carbon dioxide, and ammonia and a second stream (5) containing essentially said solvent and said diolefin, said extractive distillation step being operated at a temperature at which ammonium carbonate dissociates into ammonia and carbon dioxide, cooling said first stream to a temperature at which ammonium carbonate can form from ammonia and carbon dioxide, separating a third stream (11) from said cooled first stream which third stream contains at least water and solvent, subjecting said second stream to a first thermal stripping step (14) that essentially separates said diolefin from said solvent to provide a fourth stream (15) that contains essentially said diolefin and a fifth stream (25) that contains essentially diolefin lean solvent, said first stripping step being operated at a temperature at which ammonium carbonate dissociates into ammonia and carbon dioxide, cooling said fourth stream to a temperature at which ammonium carbonate can form, separating a sixth stream (21) from said cooled fourth stream which sixth stream contains at least water and a minor amount of solvent and diolefin, subjecting at least one of said third and sixth streams to a second thermal stripping step (32) that separates solvent and hydrocarbons from water to form a seventh stream (33) containing at least solvent and hydrocarbons and a separate eighth stream (34) that contains essentially water, said second thermal stripping step being operated at a temperature at which ammonium carbonate dissociates into ammonia and carbon dioxide, cooling said seventh stream to a temperature at which ammonium carbonate can form, separating a ninth stream (39) from said cooled seventh stream which ninth stream contains at least water, solvent and hydrocarbons, returning said ninth stream as feed to said first thermal stripping step, adding to said process at least one base compound in an amount sufficient to 1) form a stable carbonate salt with carbon dioxide which stable salt will not dissociate at the operating temperatures of said extractive distillation step and said first and second thermal stripping steps, and 2) essentially exclude the formation of ammonium carbonate in said process, and removing at least part of said stable carbonate salt from said process.

2. The process of claim 1 wherein said at least one base compound is added to at least one of 1) said diolefin lean solvent before it enters said extractive distillation step, 2) said third stream, 3) said sixth stream, 4) said third and sixth streams combined, 5) said cooled seventh stream, and 7) said eighth stream.

3. The process of claim 1 wherein said stable carbonate salt is removed with a purge stream that is removed from said eighth stream.

4. The process of claim 1 wherein said eighth stream is employed as a water wash stream for said cooled first and fourth streams, the wash water from at least one of said water washes contains at least one of solvent and hydrocarbons, and said wash water is employed as feed to said second thermal stripping step along with at least one of said third and sixth streams.

5. The process of claim 1 wherein said stable carbonate salt is formed by adding at least one base compound selected from the group consisting of sodium hydroxide and potassium hydroxide.

6. The process of claim 1 wherein said at least one base compound is added to at least one process stream in an amount of from about 4 ppm to about 0.4 weight percent based on the total weight of said at least one process stream.

7. The process of claim 1 wherein said solvent tends to form ammonia under said extractive distillation conditions.

8. The process of claim 7 wherein said diolefin is butadiene, said solvent is acetonitrile.

9. The process of claim 1 wherein said temperature at which ammonium carbonate dissociates is in the range of from about 120 to about 140 F.

* * * * *